US007153691B2

(12) United States Patent
Ferguson

(10) Patent No.: US 7,153,691 B2
(45) Date of Patent: Dec. 26, 2006

(54) METHOD OF IDENTIFYING AND ASSESSING DNA EUCHROMATIN IN BIOLOGICAL CELLS FOR DETECTING DISEASE, MONITORING WELLNESS, ASSESSING BIO-ACTIVITY, AND SCREENING PHARMACOLOGICAL AGENTS

(75) Inventor: Gary William Ferguson, Burnaby (CA)

(73) Assignee: G6 Science Corp., Burnaby (CA)

( * ) Notice: Subject to any disclaimer, the term of this patent is extended or adjusted under 35 U.S.C. 154(b) by 478 days.

(21) Appl. No.: 10/293,609

(22) Filed: Nov. 13, 2002

(65) Prior Publication Data
US 2004/0092026 A1 May 13, 2004

(51) Int. Cl.
G01N 33/52 (2006.01)
(52) U.S. Cl. .................. 436/63; 436/164; 436/166; 435/6
(58) Field of Classification Search .................. 436/63, 436/117, 164, 166, 17; 435/6
See application file for complete search history.

(56) References Cited

U.S. PATENT DOCUMENTS

| | | | |
|---|---|---|---|
| 3,957,583 A | 5/1976 | Gibson | |
| 5,016,283 A | 5/1991 | Bacus | |
| 5,168,066 A | 12/1992 | Zahniser | |
| 5,206,244 A | 4/1993 | Zahler | |
| 5,485,527 A | 1/1996 | Bacus | |
| 5,556,750 A | 9/1996 | Modrich | |
| 5,633,945 A | 5/1997 | Kamentsky | |
| 5,643,556 A | 7/1997 | Gilchrest | |
| 5,670,621 A | 9/1997 | Donahue | |
| 5,773,219 A | 6/1998 | Sanford-Mifflin | |
| 5,784,162 A * | 7/1998 | Cabib et al. ................. | 356/456 |
| 5,849,595 A | 12/1998 | Alfano | |
| 5,862,304 A | 1/1999 | Ravdin | |
| 5,871,917 A | 2/1999 | Duffy | |
| 5,889,881 A | 3/1999 | MacAulay | |
| 5,919,621 A | 7/1999 | Brown | |
| 5,936,064 A | 8/1999 | Baxter | |
| 5,942,410 A | 8/1999 | Lam | |
| 5,989,811 A | 11/1999 | Veltri et al. | |
| 5,989,816 A | 11/1999 | Van Houten | |
| 6,026,174 A | 2/2000 | Palcic | |
| 6,035,258 A | 3/2000 | Freed | |
| 6,215,892 B1 | 4/2001 | Douglass | |
| 6,271,035 B1 | 8/2001 | Deka | |
| 6,287,521 B1 | 9/2001 | Quay | |
| 6,316,189 B1 | 11/2001 | Haddad | |
| 6,348,325 B1 | 2/2002 | Zahniser | |
| 6,388,809 B1 | 5/2002 | MacAulay | |
| 6,391,026 B1 | 5/2002 | Hung | |
| 6,451,555 B1 | 9/2002 | Duffy | |
| 6,454,705 B1 | 9/2002 | Cosentino | |
| 6,455,593 B1 | 9/2002 | Grimley | |

2004/0042646 A1 * 3/2004 MacAulay et al. ......... 382/129

FOREIGN PATENT DOCUMENTS

WO         97/43732     * 11/1997
WO     WO 00/45166        8/2000

OTHER PUBLICATIONS

Soames, Feulgen Hydrolysis Profiles and Acid-labile DNA in Oral Squamous Cell Carcinoma, Oral Oncol., Eur. J. Cancer vol. 318, No. 4, pp. 222-226 (1995).
Sincock, A Semi-Automated Procedure for Aiding the Diagnosis of Cervical Neoplasms Based on the Measurement of Acid-Labile DNA in Exfoliated Cells, Eur. J. Cancer: 31. 733-36 (1983).
Sincock., Quantitative Assessment of Cervical Neoplasms by Hydrolyzed DNA Assay, The Lancet, Oct. 42, 1987.
Sincock, Semiautomated Measurement of Rapidly Hydrolyzed DNA in the Diagnosis of Mammary Carcinoma, Cancer 57:1-5, Jan. 1, 1986.
Sincock, Semi-Automated Diagnosis of Cervical Intra-Epithelial Neoplasia Grade 2 by the Measurement of Acid Labile DNA in Cytologically Normal Nuclei, Cancer 58:83-86, Jul. 1, 1986.
Petrakis, Physiologic, biochemical, and cytologic aspects of nipple aspirate fluid, Breast Cancer Research & Treatment 8:7-19 (1986).
Partington, Quantitative Determination of Acid-Labile DNA in Cervical Intraepithelial Neoplasia, Cancer 67:3104-09 (Jan. 15, 1991).
Ogden, The Effect of Distant Malignancy Upon Quantitative Cytologic Assessment of Normal Oral Mucosa, Cancer 65:477-80 (Feb. 1, 1990).

(Continued)

Primary Examiner—Maureen M. Wallenhorst
(74) Attorney, Agent, or Firm—Trexler, Bushnell, Giangiorgi, Blackstone & Marr, Ltd

(57) ABSTRACT

The present invention is a method of identifying and assessing DNA euchromatin in biological cells. The amount and/or distribution of DNA euchromatin generally relates to RNA/protein synthesis, which may change in certain conditions, such as disease, and/or cellular response to environmental and/or chemical agents. The present invention detects the potential presence of disease by assessing DNA euchromatin in ostensibly normal cells and similarly provides means to monitor and assess treatment response. The present invention may also be used to assess how application (or removal) of influences, such as environment, radiation, chemical agents, medications, herbs, vitamins, etc., interact to effect cells, establishing uses in monitoring wellness and pharmacological screening. Additional uses include assessing age related disorders, allergies, infections, Alzheimer's disease, 'Time of Death', chronic fatigue syndrome, etc. The method may be advantageously applied to biological cells including micro-organisms, plants, animals, or cultured cells, alone or in conjunction with other markers.

44 Claims, 4 Drawing Sheets

OTHER PUBLICATIONS

Millett, Feulgen-hydrolysis profiles in cells exfoliated from the cervix uteri: a potential aid in the diagnosis of malignancy, J. Clin. Pathol. 1982:345-49.

Mikel, A Comparative Study of Quantitative Stains for DNA in Image Cytometry, Analytical and Quantitative Cytology and Histology vol. 13., No. 4 (Aug. 1991).

Leif, Centrifugal Cytology of Nipple Aspirate Cells, Acta Cytological Journal Vo. 24, No. 3 (May-Jun. 1980).

Klawe, Malignancy Associated Changes (MAC) in Cells of Buccal Smears Detected by Means of Objective Image Analysis, Acta Cytologica vol. 18, pp. 30-33 (1971).

Decosse, Feulgen Hydrolysis: Effect of Acid and Temperature, The Journal of Histography and Cytochemistry (1986).

Fukuda, Cytophotometry and Biological Application, Ch. 4: Biological Application of Absorbance Cytophotometry.

Fukuda, Cytophotometry and Biological Application, Ch. 3: Errors in Absorbance Cytophotometry.

Frenster, Physiology in Medicine: Gene De-Repression, New England Journal of Medicine Jun. 7, 1973.

Frenster, Repressed and Active Chromatin Isolated from Interphase Lymphocytes, Proc. N.A.S. pp. 1026-1032.

Frenster, Ultrastructural Continuity between Active and Repressed Chromatin, Nature Mar. 27, 1965.

Finch, Malignancy Associated Changes in Buccal Smears, Acta Cytologica, vol. 15, No. 1 (Jan.-Feb. 1971).

Kiellstrand, Temperature and Acid Concenctration in the Search for Optimum Feulgen Hydrolysis Conditions, The Journal of Histochemistry and Cytochemistry, vol. 25, No. 2, pp. 129-134 (1977).

Zelenin, Peculiarities of Cytochemical Properties of Cancer Cells as Revealed by Study of Deozyribonucleop(rotein Susceptibility to Feulgen Hydrolysis, The Journal of Histology and Cytochemistry, vol. 25, No. 7, pp. 580-584 (1977).

International Search Report dated Mar. 12, 2004 which issued in connection with corresponding PCT application No. PCT/CA03/01710.

PCT Written Opinion dated Aug. 12, 2004 which issued in connection with corresponding PCT application No. PCT/CA03/01710.

PCT International Preliminary Examination Report dated Mar. 4, 2005 which issued in connection with corresponding PCT application No. PCT/CA03/01710.

* cited by examiner

METHOD OF IDENTIFYING AND ASSESSING DNA EUCHROMATIN IN BIOLOGICAL CELLS FOR DETECTING DISEASE, MONITORING WELLNESS, ASSESSING BIO-ACTIVITY, AND SCREENING PHARMACOLOGICAL AGENTS

BACKGROUND OF INVENTION

Biological cells live and communicate via complex pathways, bathing in a sea of nutrients, chemicals and cellular factors as they perform their programmed duties. In some cases of disease and infection, regiments of cells are summoned to participate or otherwise bolster the body's defense mechanisms. A variety of molecules with biological activity penetrate into the cell nucleus and bind to DNA in the double-stranded state or in the single-stranded state, thereby participating in the opening or closing of DNA helices, and hence are involved in the up or down regulation of RNA/protein synthesis. In the face of disease, cells may respond in dramatic fashion, abandoning present duties to adopt new roles, sometime differentiating to become antibody-producing or scavenger cells. Yet other cells performing routine and beneficial housekeeping tasks such as cellular repair may be subverted to produce factors that assist in the growth or vascularization of cancerous tissue.

At times, cells adjacent or distant from diseased tissue may be alerted to the presence of disease by cellular factors circulating in the system. However, instead of responding in an obvious manner, various cells may undergo a subtle reorganization of DNA, which may be observed in both condensed chromatin (heterochromatin) and more loosely-packed DNA (euchromatin) which may be currently active in RNA/protein synthesis. Typically, to observe DNA by these methods requires that DNA be visually enhanced, which is accomplished with staining. However, to measure the amount of DNA and/or the distribution of DNA requires that DNA be stained, stoichiometrically, that is, specifically and proportionately.

While changes in total DNA content (not associated with cell mitosis) have been used diagnostically, more recently, improved methods have been introduced to detect diseases, such as cancer, based upon configurational changes in the spatial distribution of DNA. One such method utilizes what are called malignancy-associated changes ("MAC") which are sometimes observed in the presence of diseases, such as cancer, and provide one example of a generally non-specific response to cell factors.

Malignancy-associated changes (MAC) are considered to be subtle changes observed primarily in the distribution of DNA in ostensibly normal cells. Assays based on MAC differ significantly from measurements based on total DNA or genetic tests which detect specific DNA alterations, since unlike MAC, these assays rely on abnormal cells. Therefore, while malignancy-associated changes (MAC) may be less specific than genetic tests, they provide a means to detect the presence of disease, or DNA distributional changes in ostensibly normal cells. Advantages of MAC include the ability to utilized cells from associated or non-associated tissue to detect diseases such as cancer.

Associated tissue would be a sample that may reasonably be expected to contain ostensibly normal cells from the tissue being tested. For example, if lung sputum was used to screen for lung cancer, it would be considered to be an associated tissue (contains exfoliated lung cells), as would nipple aspirates for the detection of breast cancer. A discussion of nipple aspirates may be found in Petrakis, "*Physiologic, Biochemical, And Cytologic Aspects Of Nipple Aspirate Fluid*", with additional discussion provided by Leif in "*Centrifugal Cytology Of Nipple Aspirate Cells*". Alternatively, if a more accessible or convenient source of cells (which may have been alerted to the presence of disease via chemical messages), which is unlikely to contain a significant number of cells from the tissue under test, this would be considered to be a non-associated tissue. For example, if cells derived from the oral cavity (buccal mucosa) were used for an assay to detect lung cancer, then buccal mucosa would be considered to be a non-associated tissue.

One potential limitation of the MAC paradigm is that it is based upon staining substantially all the DNA in the cell nucleus, which may obscure cellular activity associated with RNA/protein synthesis, as contemplated by the present invention.

It would therefore be advantageous to provide a disease detection method, based on ostensibly normal cells, which offers increased sensitivity to the presence of disease. The present invention is such a method and provides a means to detect and monitor disease based on changes measured in the amount of DNA euchromatin and/or the distribution of DNA euchromatin, thus providing an indirect way of assessing a cell's current potential for RNA/protein synthesis.

As used herein, "cell response factor" (CRF) means any cell response to an outside influence such as proteins, chemicals, stress (e.g. heat, magnetic or electromagnetic energy, pressure, or other forms of energy), medication, vitamins, herbs, cosmetics, or environmental conditions, which may be measured or observed in the amount of DNA euchromatin and/or the distribution of DNA euchromatin in biological cells. While the concentration and degree of stress encountered by cells, in vivo, may be limited, the present method may be used alone or in combination with other assays or biomarkers in plant cells, cultured cells, stem cells, bacteria, or any other source of biological cells, living or dead.

Generally DNA euchromatin is that unique combination of DNA, RNA and proteins that allow the magnificent cellular program within the cell nucleus to proceed with accuracy, safety and flexibility. As used herein, "euchromatin" or "DNA euchromatin" means that portion of DNA in biological cells that appears to be transcriptionally active. This definition includes those DNA portions that are loosely coiled. Approximately 10 percent of DNA euchromatin may present in cells as 10 nm fibers, with some open strands approximately 4 nm in diameter. The balance of DNA euchromatin typically appears as a 20 to 30 nm fibers. Conversely, heterochromatin is more condensed than euchromatin, is not transcriptionally active, and may be further coiled to form fibers of in the range of 300 nm in diameter.

In biology, since the discovery of DNA and its association with diseases, such as cancer, substantial efforts have been made to develop methods to quantify the DNA content of biological cells. More recently, cytologists have been provided with tools such as image cytometers, densitometers, flow cytometers and laser scanning cytometers, to measure cell features such as size, shape, DNA content and DNA distribution. To measure total cellular DNA by image cytometry requires that DNA first be stained, stoichiometrically, that is, proportionately to the amount of DNA. The Feulgen method is one such DNA staining method and the contrast agent is often pararosaniline or a thiazine derivative. The most common stains used in Feulgen procedures include pararosaniline, azure A, thionin, and acriflavine (which may be utilized in both absorbance and fluorescent staining procedures). Additional details regarding useful DNA stains may be found in Mikel's publication entitled, "*A Comparative study of quantitative stains for DNA in image cytometry*".

To stain DNA using the Feulgen method, DNA is first hydrolyzed, typically using hydrochloric acid, which specifically and quantitatively removes purine bases, leaving the pyrimadine-sugar linkage of the DNA intact. Stripped deoxyribose sugars expose aldehyde groups along the backbone of the DNA which are subsequently coupled to Schiff's reagents to produce a staining intensity, which, ideally, is directly proportional to the amount of DNA in the cell.

Feulgen staining methods evolved over several decades and during this development a number of variables that influence DNA staining were identified. These include cell fixation, reaction temperature, hydrolysis time, acid concentration, tissue type and chromatin compactness. Two general Feulgen staining methods for DNA became accepted, differing primarily in the conditions for DNA hydrolysis. The first method advocates DNA hydrolysis at room temperature (25° C.) at a relatively high acid concentration (5 N HCL). The second adopts a reaction temperature of 60° C. using 1 N HCL.

Briefly, cells deposited on a microscope slide are immersed under the hydrolysis conditions described above, typically for between 20 and 65 minutes. During this time, ideally, all the purine bases (adenine and guanine) are removed from the DNA. This reduced state may be relatively stable over some period of time after which continued acid hydrolysis causes degradation of the DNA, as may be indicated by a decrease in optical density.

While studying DNA hydrolysis, some researchers observed that a fraction of the DNA appears to stain quickly. They called this portion of DNA, acid-labile, and began to study the kinetics of acid hydrolysis more closely, hoping to use the acid-labile characteristics to differentiate normal cells from diseased. Further discussion may be found in Sincock, "*Semi-Automated Diagnosis Of Cervical Intra-Epithelial Neoplasia Grade 2 By The Measurement Of Acid Labile DNA In Cytologically Normal Nuclei*", Soames, "*Feulgen hydrolysis profiles and acid-labile DNA in oral squamous cell carcinoma*", Finch, "*Malignancy Associated Changes In Buccal Smears*", Klawe, "*Malignancy-Associated Changes (MAC) In Cells Of Buccal Smears Detected By Means Of Objective Image Analysis*", Partington, "*Quantitative Determination Of Acid-Labile DNA In Cervical Intraepithelial Neoplasia-A Potential Aid In The Diagnosis Of Malignancy*", Ogden, "*The Effect Of Distant Malignancy Upon Quantitalive Cytologic Assessment Of Normal Oral Mucosa*", Sincock, "*A Semi-Automated Procedure For Aiding The Diagnosis Of Cervical Neoplasms Based On The Measurement Of Acid-Labile DNA In Exfoliated Cells*", Sincock, "*Semiautomated Measurement Of Rapidly Hydrolyzed DNA In The Diagnosis Of Mammary Carcinoma*", and Sincock, "*Quantitative Assessment Of Cervical Neoplasia By Hydrolysed DNA Assay*".

Unfortunately, no widely accepted assay based on the total amount of acid-labile DNA evolved from these studies. Limitations include the need to prepare multiple slides, under strict conditions, therefore increasing the time, cost and complexity of these potential methods. In addition, as will be discussed further, these applications, like MAC assays, may have reduced sensitivity to cellular changes associated with RNA/protein synthesis.

Another aspect of DNA that attracted attention was its spatial distribution in cell nuclei. In the late 1950s Nieburgs identified subtle cellular changes which he associated with disease.

When first described, malignancy-associated changes (MAC) were a curiosity. Nieburgs; "*Recent Progress In The Interpretation Of Malignancy Associated Changes (MAC)*", ACTA Cytologica 1968, Vol. 12, No.6. Various researchers sought to duplicate Neiburgs' work. Only recently has the MAC paradigm resurfaced and an automated measurement method been suggested. While still controversial, MAC are described as subtle changes measured in the DNA distribution of ostensibly normal cell nuclei and are associated with non-specific and potentially systemic responses to tumor or other cell factors. Hence, the present invention adopts the general term "cell response factor" or "CRF" as convenient nomenclature.

MAC methods are described in U.S. Pat. No. 5,889,881 and further in U.S. Pat. No. 6,026,174. In addition, co-pending U.S. patent application Ser. No. 10/232,698, to MacAulay, Ferguson et al., filed on approximately Aug. 29, 2002, entitled, "*Computerized methods and systems related to the detection of malignancy-associated changes (MAC) to detect cancer*", further describes methods to improve the assessment of MAC based on the normalization of digital images prior to cell feature calculation, thereby maintaining the discriminating power of these cell features. The present invention includes embodiments that support image normalization for use in the determination of a CRF or other descriptors of DNA euchromatin.

DNA euchromatin may be preferentially stained and assessed. In some instances, for example when cells are deposited on a receiving surface, such as a microscope slide, the same cells may be further hydrolyzed and the remaining DNA stained. This provides a means to compare the amount and distribution of DNA euchromatin with total cellular DNA and its distribution, on a cell-by-cell basis. The amount as well as the location sites of DNA synthesis measured in this manner may provide additional diagnostic information. These abilities may have increased importance as other microscopic methods gain broader acceptance. For example, confocal microscopy provides the ability to collect a plurality of cellular image slices for three dimensional reconstruction. (e.g. U.S. Pat. No. 6,388,809) The caveat regarding receiving surface serves as a reminder that other measurement tools, such as flow cytometers, may provide the ability to measure DNA and related cellular features as contemplated, herein. These systems maintain cells in a fluid environment, typically directing them to a sensor that often includes a laser. After analysis by flow cytometry, unless special efforts, such as cell sorting, are utilized, the biological cells used in the assay are typically lost.

Decades of effort has gone into optimizing Feulgen methods to stain substantially all DNA and although Feulgen methods do not typically provide for preferentially staining DNA euchromatin, they do offer a step in the process which may be exploited to advantage for the present invention. This step relates to DNA hydrolysis, whereby acid is used to selectively and specifically strip away purine bases from the DNA backbone. Typically a DNA absorbance stain such as pararosaniline or a thiazine derivative such as thionin is used as a contrast agent. Other DNA stains include propidium iodide, adenine-thiamine selective stains such as DAPI, Hoechst (33342 and 33258), SYTOX (blue, green or orange), and cytosine-guanine stains such as chromomycin A3 and mithramycin. These stains, however, do not typically differentiate between dense chromatin and euchromatin.

However, in future it may be possible to block certain DNA sites and subsequently exploit one or more of these DNA fluorescent stains for the present invention. New methods to rapidly stain nucleic acids (e.g. U.S. Pat. No. 6,271,035) are being introduced and microwaves have also been employed to facilitate staining.

Another method to assess DNA and DNA euchromatin is based on the methylated state of DNA. These techniques are relatively complex and typically require that DNA be removed from cells and be further manipulated using PCR or other techniques. Again, DNA methods based on methylated state function optimally on abnormal cells which may be difficult to obtain or access, sometimes requiring a biopsy procedure.

It would therefore be advantageous to provide a simple method of detecting and monitoring disease that could be applied to readily accessible, ostensibly normal cells. While tissue obtained from biopsies may be employed for the present invention, for high volume applications, such as, at risk population screening, it may be preferable to use scraping of cells from accessible body cavities (e.g cervix), body fluids (e.g. blood or urine), aspirates (e.g. breast or fine needle), washings (e.g. bronchial-lavage or bladder washings), or samples typically rich in exfoliated cells (e.g. lung sputum or cells from the oral cavity). The present method may also prove useful for detecting or monitoring disease where specific markers or disease mechanisms are not yet fully understood, for example, auto-immune diseases, stress disorders, chronic fatigue syndrome, allergies, age related disorders, infections, or other degenerative diseases such as Alzheimer's. Similarly, the complex interaction of vitamins, herbs, food supplements, medications and exposure to various forms of energy from sunlight to cell phones may also cause cellular changes observable in DNA euchromatin. These may be utilized, for example, in monitoring a diseases response to treatment, assessing wellness, evaluating bioactivity or screening pharmacological agents. Generally speaking, anything that causes or is associated with changes in RNA/protein synthesis in cells is of potential interest, whether these changes occur in microorganisms, plants or humans. In addition, it may be useful to use DNA euchromatin assessments to further characterize cell death (apoptosis) or other biological processes, or as a basis for new assays, such as determination of 'time of death' by sampling dead or dying cells, for example.

In the mid 1960s, Decosse and Aiello published the paper entitled "*Feulgen Hydrolysis: Effect Of Acid And Temperature*" describing DNA acid hydrolysis and concluding that Feulgen hydrolysis at room temperature (26° C.) using 5.0N HCL was essentially equivalent DNA acid hydrolysis at 60° C. using 1.0N HCL. The authors noted that the 120-minute plateau provided by the former at room temperature was superior to the 20-minute stability observed at 60° C. Additionally, they concluded that depurination (removal of purine bases from DNA) depended primarily on acid concentration and that subsequent DNA degradation is dependent primarily on heat rather than acid. Accordingly, the reaction temperature and conditions for hydrolysis go against what is discussed in prior art. Some embodiments of the present invention identify DNA euchromatin for assessment by preferential staining, for example, lowering the reaction temperature for acid hydrolysis of DNA by approximately 10 degrees C. appears to slow hydrolysis (at a given acidity) four fold, thus providing improved control over DNA staining and more particularly facilitates preferential staining of DNA euchromatin Later, Fukuda summarized the history of DNA acid hydrolysis and staining in "*Errors in Absorbance Cytophotometry*" with additional discussion in "*Biological Application Of Absorbance Cytophotometry*". Similar conclusions were observed by Zelenin in "*Peculiarities Of Cytochemical Properties Of Cancer Cells As Revealed By Study Of Deoxribonucleoprotein Susceptibility To Feulgen Hydrolysis*" and Kjellstand in "*Temperature And Acid Concentration In The Search For Optimum Feulgen Hydrolysis Conditions*".

More recently, U.S. Pat. No. 5,016,283, to Bacus, entitled, "Methods and apparatus for immunoploidy analysis", teaches acid hydrolysis for 60 to 75 minutes in 5 N HCL followed by thionin staining for 60 minutes. Similarly, U.S. Pat. No. 5,485,527, to Bacus, entitled, "Apparatus and method for analysis of biological specimens", teaches DNA acid hydrolysis in 5 N HCL for 60 to about 75 minutes. And U.S. Pat. No. 5,942,410, to Lam, entitled, "Composition and method for staining cellular DNA, comprising thiazine derivative metabisulfite and method", summarizes the prior art for DNA staining and further promotes a DNA hydrolysis time of 60 minutes in 5 N hydrochloric acid followed by 75 minutes of staining. DNA staining is also discussed in U.S. Pat. No. 6,348,325, to Zahniser, entitled "Cytological stain composition."

Current devices and methods to measure and exploit DNA measurements are taught in U.S. Pat. No. 5,889,881, to MacAulay, entitled, "Method and apparatus for automatically detecting malignancy-associated changes", and also U.S. Pat. No. 6,026,174, to Palcic, entitled, "System and method for automatically detecting malignant cells and cells having malignancy-associated changes". This prior art teaches both the use of DNA content (ploidy) and MAC (subtle changes reflected primarily in the distribution of DNA within ostensibly normal cells) for disease detection as well as discussing a variety of useful cell features. In addition, DNA descriptors for disease detection using MAC are further discussed in co-pending U.S. patent application Ser. No. 10/232,698, to MacAulay, Ferguson et. al., filed on approximately Aug. 29, 2002, entitled, "Computerized methods and systems related to the detection of malignancy-associated changes (MAC) to detect cancer", which among other things discusses DNA measurements, cellular features and methods to normalize cell features by first normalizing the digital images of cells.

This MAC prior art also discusses utilizing combinations of cellular features and reducing DNA measurements to a value, such as MAC score, which like CRF, may be considered to be a cell response factor. Accordingly, this MAC prior art and other prior art cited in this application are included by reference, herein.

Today it is understood that DNA helices must undergo localized strand separation at particular gene loci for the onset of RNA or DNA synthesis. Such activity is observed during both gene transcription and replication. By far, the vast majority of DNA in various cell types remains inactive, after cellular programming. Accordingly, it may be useful to measure both total DNA and DNA euchromatin and express these values as a ratio, such as percent DNA euchromatin.

In related studies, investigators considered that an increase in acid-labile DNA may be associated with malignancy. Acid-labile DNA was explored by Sincock. He suggested lower hydrolysis temperatures than Fukuda ("*Errors In Absorbance Cytophotometry*") and performed hydrolysis at 30° C. in 5 N HCL indicating that certain diseases (CIN 2) may cause increase the percentage of cells in S-phase (the phase during which cells in mitosis copy substantially al of their DNA). Previously, Millett in "*Feulgen-Hydrolysis Profiles In Cells Exfoliated From The Cervix Utero. A Potential Aid In The Diagnosis Of Malignancy*" also suggested lower temperatures than those used in previous studies and opted for 5 N HCL at room temperature. Similarly with, Partington made this suggestion in "*Quantitative determination of acid-labile DNA in cervical intraepithelial neoplasia*". In Soames' 1995 paper entitled "*Feulgen Hydrolysis Profiles And Acid-Labile DNA In Oral Squamous Cell Carcinoma*", hydrolysis conditions were 5 N HCL at room temperature. While Kjellstand, cited above, discusses a wide range of temperature and acidity for Fuelgen hydrolysis, he does not discuss or acknowledge advantages associated with partial DNA staining and accordingly provides conclusions and recommendations that go against the methods and embodiments of the present invention.

U.S. Pat. No. 5,871,917, to Duffy, entitled, "Identification of differentially methylated and mutated nucleic acids", among other things, discusses methods for detecting and isolating genomic DNA fragments that are near coding and regulatory regions of genes. It is noted that DNA is frequently methylated in tumor cells.

U.S. Pat. No. 6,451,555, to Duffy, entitled, "Nucleic acids that encode testes specific protease and detect DNA hypomethylated in cancer cells", discusses methods for detecting and isolating genomic DNA fragments which are near coding and regulatory regions of genes and sensing the extent that DNA is methylated in various regions.

U.S. Pat. No. 5,556,750, to Modrich, entitled, "Methods and kits for fractionating a population of DNA molecules based on the presence or absence of a base-pair mismatch utilizing mismatch repair systems", discusses contacting and comparing DNA strands to detect base pair mismatches using DNA protein complex formation as an indicator.

While the human genome project addressed essentially a linear problem (nucleic acid sequences), proteins present a three-dimensional problem deriving much of their functionality from shape and exposed or charged regions that allow them to react and interact with other chemicals and proteins, often with high specificity. Accordingly, while the present invention does not seek to measure specific aberrations, such as base-pair mismatch, it does seek to measure changes related to RNA/protein synthesis at a cellular level.

U.S. Pat. No. 5,206,244, to Zahler, entitled, "Hydromethyl (methylenecyclopentyl) purines and pyrimidines", discusses methylenation reagents and various factors related to protein synthesis and more particularly methylated state of the building blocks of DNA—the purines, adenine and guanine, and pyrimadines, cytosine and thymine.

U.S. Pat. No. 5,936,064, to Baxter, entitled "Acid-labile subunit (ALS) of insulin-like growth factor binding protein complex", discusses a specific acid-labile protein and its fragments. This prior art relates generally to acid-labile proteins and means to assess proteins states based on their amino acids.

U.S. Pat. No. 5,643,556, to Gilchrest, entitled "Stimulation of tanning by DNA fragments or single-stranded DNA", among other things discusses damage to skin from exposure to agents such as ultraviolet light. While this patent (556) is interested in melanogenesis-stimulation, the present invention could be used to help assess if various agents are associated with a cellular response.

U.S. Pat. No. 5,773,219, to Sanford-Mifflin, entitled "Process for detecting Alzheimer disease using cultured cells", uses DNA assessments such as gaps and breakage. Such changes may also be inferred by DNA euchromatin assessments as contemplated herein.

U.S. Pat. No. 5,670,621, to Donahue, entitled, "DNA structure specific recognition protein complexes", among other things discusses DNA structure, a mammalian cellular factor and drug responses.

U.S. Pat. No. 6,455,593, to Grimley, entitled "Method of dynamic retardation of cell cycle kinetics to potentiate cell damage", describes cellular restraining agents and targeted cytotoxic insults. Again, the present invention may be used independently or in combination to help assess or guide discovery of various agents.

U.S. Pat. No. 6,391,026, to Hung, entitled, "Methods and systems for treating breast tissue", describes diagnostic methods and energy forms used to treat breast disease. The present invention could be used for example to assist in monitoring the effectiveness of such treatment.

U.S. Pat. No. 6,287,521, to Quay, entitled "Devices and methods for obtaining and assaying mammary fluid samples for evaluating breast diseases, including cancer", discusses obtaining biological samples containing cells, such as mammary fluid. As described herein, breast aspirates would be considered an associated tissue for detecting breast cancer as contemplated by the present invention.

U.S. Pat. No. 6,035,258, to Freed, entitled, "Method for correction of quantitative DNA measurements in a tissue section", further discusses Feulgen staining of histological tissue. As desired, similar methods could be applied to the present method.

U.S. Pat. No. 5,989,816, to Van Houten, entitled, "Method to detect DNA damage and measure DNA repair rate", discusses DNA assays to measure DNA repair and monitor the efficacy of various therapies. The present invention may be used to support such assays.

U.S. Pat. No. 5,633,945, to Kamentsky, entitled, "Accuracy in cell mitosis analysis" describes DNA staining with fluorescent stains and measurement using a cytometer. Accordingly, DNA measurements and assessment of the cell cycle are discussed and plotted as for example in FIGS. 3, 14, 15 and 16 of that patent. Accordingly, DNA histograms are represented in as prior art in FIG. 1a of the present invention.

U.S. Pat. No. 6,215,892, to Douglass et. al., entitled, "Method and apparatus for automatic image analysis of biological specimens", discusses an image cytometer, which may be used to measure DNA.

U.S. Pat. No. 5,849,595, to Alfano, entitled, "Methods for monitoring the effects of chemotherapeutic agents on neoplasmic media", among other things, discusses agents such as retinoic acid and means to gauge effects at a cellular level. Monitoring the effects of various agents is contemplated for the present invention.

U.S. Pat. No. 3,957,583, to Gibson, entitled, "Apparatus and process for determining the susceptibility of microorganism to antibiotics", discusses some of the issues and interests in assessing bio-activity and pharmacological screening as well as various culture media.

U.S. Pat. No. 5,016,283, to Bacus, entitled, "Methods and apparatus for immunoploidy", discusses another configuration of image cytometer as well as methods to stain and measure DNA (e.g. Feulgen), sometimes in conjunction with other bio-indicators, such as estrogen. In addition, this patent (283) discusses various ways of expressing DNA content, for example, using a DNA calibrator and converting DNA values to picograms. As desired such conversion could be applied to DNA euchromatin as contemplated herein.

U.S. Pat. No. 5,485,527, to Bacus, entitled, "Methods and apparatus for analysis of biological specimens" further discusses DNA measurements, providing yet another example of established and suggested DNA staining (e.g. using thionin) and more particularly DNA hydrolysis conditions.

DNA staining is discussed in further detail in U.S. Pat. No. 5,168,066, to Zahniser, entitled, "Thionin staining and imaging technique", and further discusses DNA staining with thionin as well as counter staining various cellular components such as the cytoplasm.

U.S. Pat. No. 5,942,410, to Lam, entitled, "Composition and method for staining cellular DNA, comprising thiazine derivative metabisulfite and methanol or ethanol", further discusses DNA and Feulgen staining methods.

U.S. Pat. No. 5,862,304, to Ravidin, entitled, "Method for predicting the future occurrence of clinically occult or non-existent medical conditions", discusses data evaluation and DNA histograms for prognosis.

U.S. Pat. No. 6,454,705, to Cosentino, entitled, "Medical wellness parameters management system, apparatus and method", discusses patient monitoring and refining information to form a score, as well as discussing recognition of trends and monitory frequency. While this patent (705) describes a systematic decision making process to identify symptomatic patients, in addition, the present method may be used to identify non-specific changes (e.g. changes in RNA/protein synthesis) observed in DNA euchromatin which may be used for screening asymptomatic groups, such as current or past smokers for lung related diseases, including cancer.

SUMMARY

The present invention is a method of identifying and assessing DNA euchromatin in biological cells for detecting disease, monitoring wellness, assessing bio-activity and pharmacological screening, for example. One embodiment describes a method to detect disease and monitor a diseases response to treatment based on identifying and assessing DNA euchromatin, for example, by preferentially staining DNA in biological cells. Other embodiments provide means to identify and assess DNA euchromatin, for example, the amount of DNA euchromatin and the distribution of DNA euchromatin in individual cells, establishing an assay that generally relates to RNA/protein synthesis, which may change in certain conditions, such as disease or cellular exposure to various influences.

Accordingly, the present invention provides a method to detect the potential presence of diseases, such as cancer, by measuring DNA euchromatin which may be expressed as a value such as a CRF. Assessing DNA euchromatin in ostensibly normal cells may provide a useful adjunct to genetic tests or other assays which rely on the presence of specific or non-specific cellular abnormalities. The present invention also provides improvements in sensitivity and specificity over assays such as malignancy-associated changes (MAC). In addition, by establishing basal levels of DNA euchromatin staining for an individual or source of biological cells, the present methods provide a means to monitor changes which may be used as indications of wellness, or response to various influences, including disease treatment. For pharmacological screening or assessing bio-activity of various agents, cells may be measured before, after, during exposure or after removal of such influences to assess DNA responses observed in DNA euchromatin, for example.

DESCRIPTION OF THE PREFERED EMBODIMENTS OF THE INVENTION

Figure 1A:
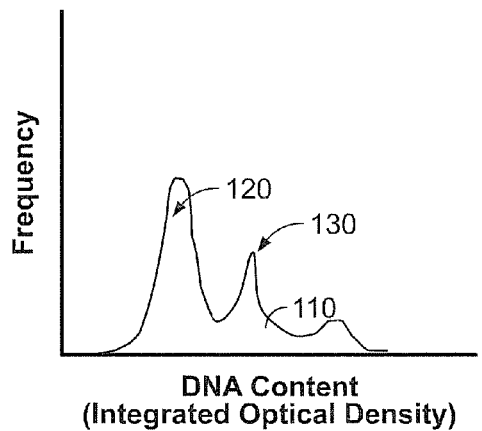
FIG. 1a (prior art) A typical DNA content histogram for a sample of epithelial cells taken from a lung cancer patient.

The organization and manner of the method of the preferred embodiments of the invention, together with further objects and advantages thereof, may best be understood by reference to the following description, taken in connection with the following drawings:

FIG. 1a (prior art) shows a typical DNA content histogram 110 for a sample of endothelial cells taken from a lung cancer patient. In this instance, a DNA aneuploid peak 130 provides diagnostic information that may identify this as a cancer. In addition, even in the absence of such a diagnostic indicator, MAC may be, and is typically assessed on ostensibly normal cells, for example those in the diploid peak 110 of DNA content histogram 110.

Figure 1B:
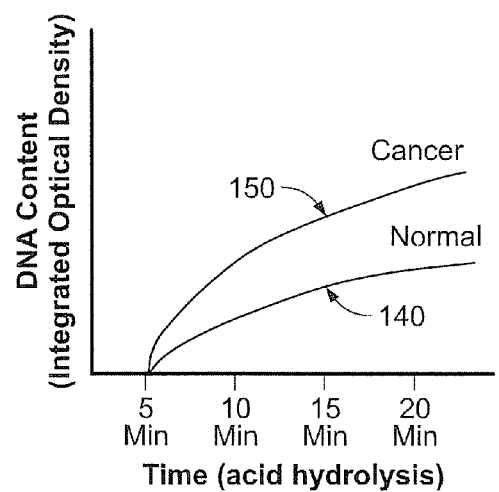
FIG. 1b (prior art) Typical time-based measurements of DNA acid-hydrolysis for a normal sample of lung endothelial cells and the acid-labile curve for lung cancer.

FIG. 1b (prior art) shows typical time based measurements of DNA acid-hydrolysis for a normal sample of lung endothelial cells 140 and the acid-labile DNA curve for lung cancer 150. Researchers noted that differences in the rate of acid hydrolysis for a fraction of DNA they called 'acid-labile', held potential diagnostic utility. Producing such data requires that multiple slides be processed (hydrolyzed for specific time intervals and stained). While this demonstrates that acid hydrolysis (DNA kinetics) may provide diagnostic information, the present invention alters the hydrolysis conditions to exploit DNA kinetics and more particularly to preferentially stain DNA euchromatin.

Figure 1C:
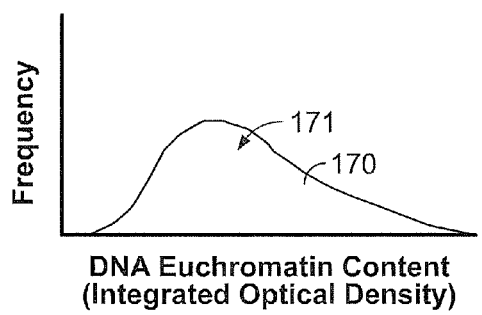
FIG. 1c A histogram of an embodiment of the present invention with normal biological cells having their DNA euchromatin preferentially stained using the Feulgen method.

FIG. 1c shows histogram 170 of the present invention with normal biological cells having their DNA euchromatin preferentially stained using the Feulgen method. The histogram shows relatively uniform DNA euchromatin staining in cells and a peak 171 indicating the range (e.g. as assessed by population statistics such as the standard deviation, slope, etc.) and degree (e.g. peak or mean staining intensity) of potential RNA/protein synthesis occurring in these cells. As previously discussed, it may also be useful to express the ratio of DNA euchromatin to total cellular DNA.

Figure 1D:
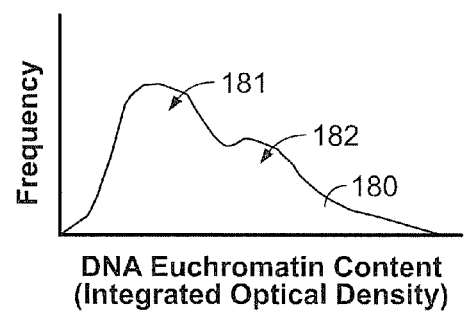
FIG. 1d A histogram of an embodiment of the present invention with preferential staining of DNA euchromatin in diseased cells.

FIG. 1d shows histogram 180 of the present invention with preferential staining of DNA euchromatin in diseased cells. Cells in region 181 show increased DNA euchromatin (more small DNA fibers that may be active in transcription) and a second minor peak 182 that may represent a subpopulation of cells having different activity (RNA/protein synthesis). Again, the ratio of DNA euchromatin to total cellular DNA may also provide diagnostic information. Such a ratio could be expressed for all cells, or for various sub-populations of cells. For example, DNA euchromatin or the DNA euchromatin ratio could be measured for a subpopulation of cells such as those cells within 2 S.D. of peak 120 of DNA content histogram 110, discussed in association with FIG. 1a. Various cellular features, such as size, shape, roundness, area, regularity, etc. are commonly used to identify cells and subpopulations of cells and may be applied accordingly.

Figure 2A:
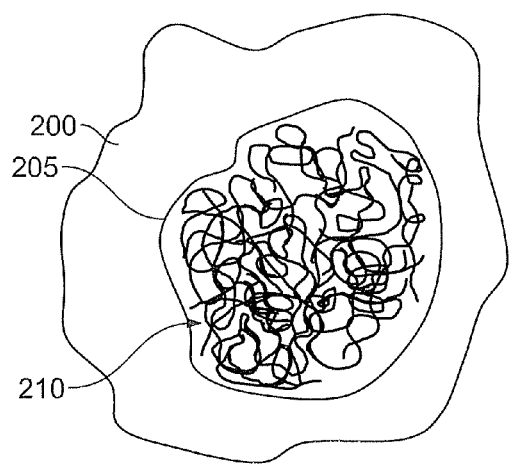
FIG. 2a (prior art) A typical endothelial cell with stained nucleus.

FIG. 2a (Prior Art) diagrammatically shows a typical endothelial cell 200 with nucleus 205 with stained DNA 210. Although regions of light and dark staining (heterochromatin) can be assessed and expressed in terms of cellular features, areas of light staining and finer threads of DNA (potential euchromatin) are obscured or these signals are partially eclipsed by overlying or adjacent dark DNA staining regions. Some of the discriminating power of MAC may be related to DNA rearrangement and hence RNA/protein synthesis. Therefore the present invention may provide similar and potentially more diagnostic sensitivity than MAC, or MAC alone.

Figure 2B:
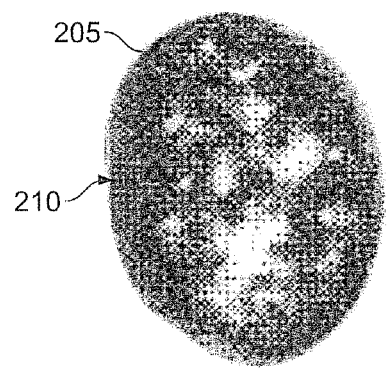
FIG. 2b: The typical endothelial cell of FIG. 2a with DNA euchromatin preferentially stained.

FIG. 2b shows a pixilated image of a cell nucleus 205 such as the cell discussed in association with FIG. 2a, with its DNA stained. Cell features such as size, shape, integrated optical density (total DNA) and other cellular features that describe the spatial distribution of DNA are commonly measured from these digital images. Examples of cellular features and their application may be found in various United States Patents cited herein, such as U.S. Pat. Nos. 5,889,881 and 6,062,174.

Figure 2C:
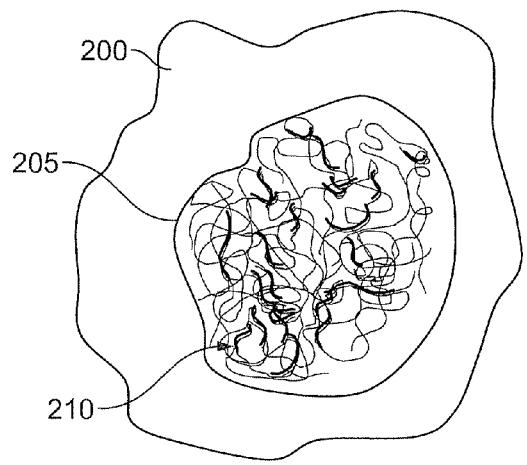
FIG. 2c: A diagrammatic representation of a typical biological cell with preferential staining of DNA euchromatin.

FIG. 2c diagrammatically shows a typical endothelial cell 200 with nucleus 205 with DNA euchromatin 220 identified by preferential staining. In this instance, the dark staining condensed DNA (heterochromatin) discussed in association with FIG. 2a has not been stained, however, DNA euchromatin 220 has been identified by preferential staining.

Figure 2D:
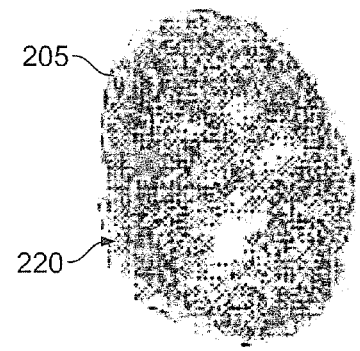
FIG. 2d: A pixilated image of a typical biological cell with preferential staining of DNA euchromatin.

FIG. 2d shows a pixilated image of a typical cell nucleus 205 having had its DNA euchromatin 220 identified by preferentially staining. The amount of DNA euchromatin and the spatial distribution of DNA euchromatin may be measured from this digital image. Fine DNA threads (approximately 10 nM in diameter with potential for some strand separation of single strand DNA of approximately 4 nM diameter) as well as DNA strands in the order of 20–30 nM in diameter are potential sites of RNA/protein synthesis. Since overall darkness also provides a useful indication of the nuclear boundary, in some instances, in addition to, or in combination with routine cellular feature measurement, other boundary methods or estimations may be used, for example, based on the approximate cell size, elliptical estimates may be fit to the data or the nucleus or cytoplasm of the cell counterstained.

In some embodiments of the present invention, diagnostic information may include DNA ratios, such as DNA euchromatin/total cellular DNA, which may also be expressed as a percentage. Also in addition, to DNA measurements on individual cells, when measured on tissue sections, the distribution of cells may provide diagnostic information regarding tissue architecture useful for example in assessing the invasiveness or staging of tumors. Accordingly, in a scene containing several to several hundred cell images, the distribution of cells having certain amounts of DNA and/or DNA euchromatin may be used potentially as a diagnostic indicator. Various techniques such as Voronoi diagrams have been used to provide descriptors of tissue architecture or cell organization in cultures. Some of the bases and applications of these techniques are discussed U.S. Pat. No. 6,453,246, to Agrafiotis, entitled "System, method, and computer program product for representing proximity data in a multidimensional space". While some of (246) is directed at descriptors of chemical structure, similar techniques could be utilized for describing DNA euchromatin distribution in a field and such use is contemplated for the present invention.

Figure 3A:
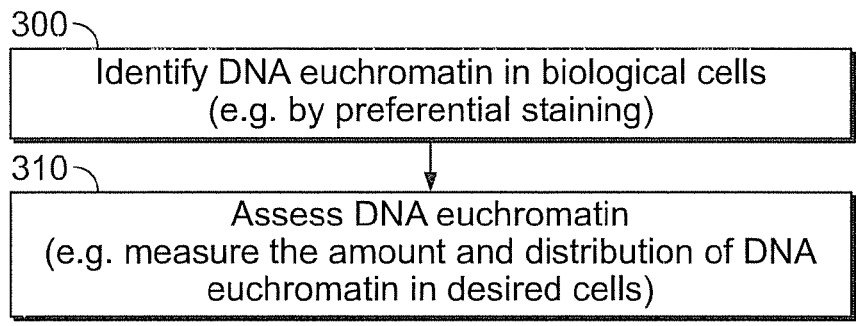
FIG. 3a A block diagram of an embodiment of the present invention.

FIG. 3a shows an embodiment of the present invention comprising the steps of collecting cells, preferentially staining DNA euchromatin 300 and measuring the amount and distribution of DNA cuchromatin 310.

Figure 3B:
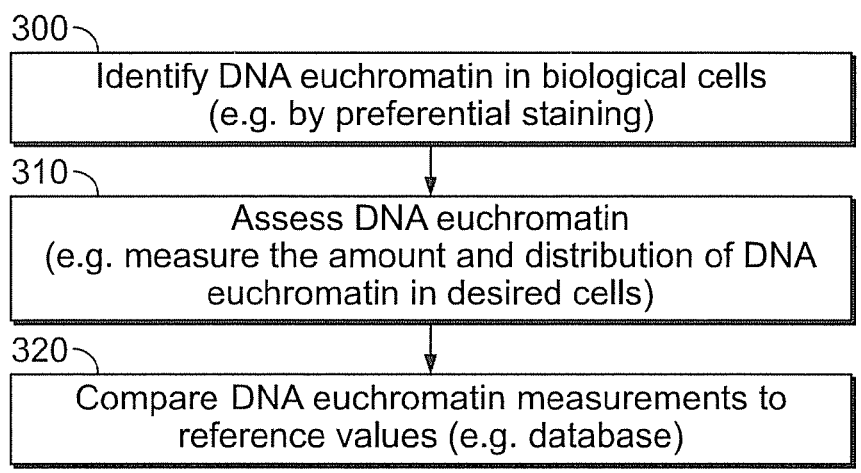
FIG. 3b: A block diagram of an embodiment of the present invention.

FIG. 3b shows another embodiment of the present invention discussed in association with FIG. 3a, further comprising comparing the amount and distribution of euchromatin to a reference value 320, which can be a database.

Figure 3C:
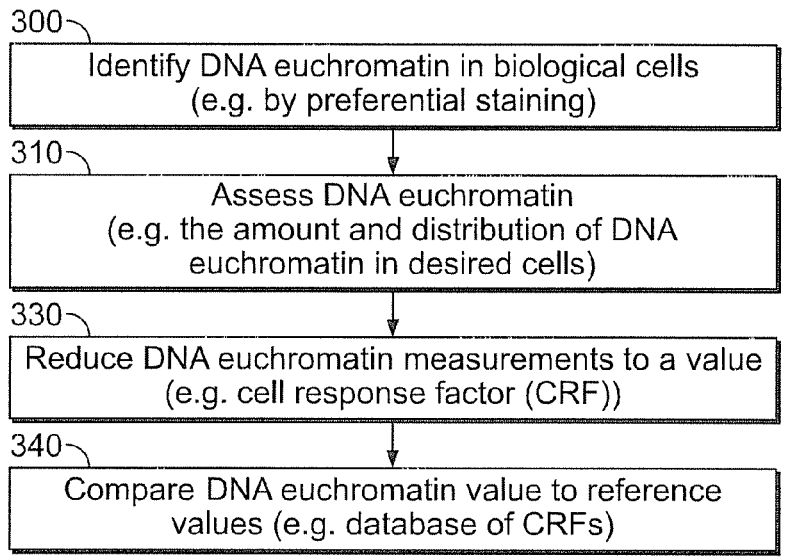
FIG. 3c: A block diagram of an embodiment of the present invention.

FIG. 3c shows yet another embodiment of the present invention discussed in association with FIG. 3a and FIG. 3b, further comprising expressing the results of various calculations 330 such as a cell response factor (CRF) and DNA ratios and comparing these results to a database 340. The database may contain the results obtained for a plurality of normal and diseased samples.

Figure 3D:
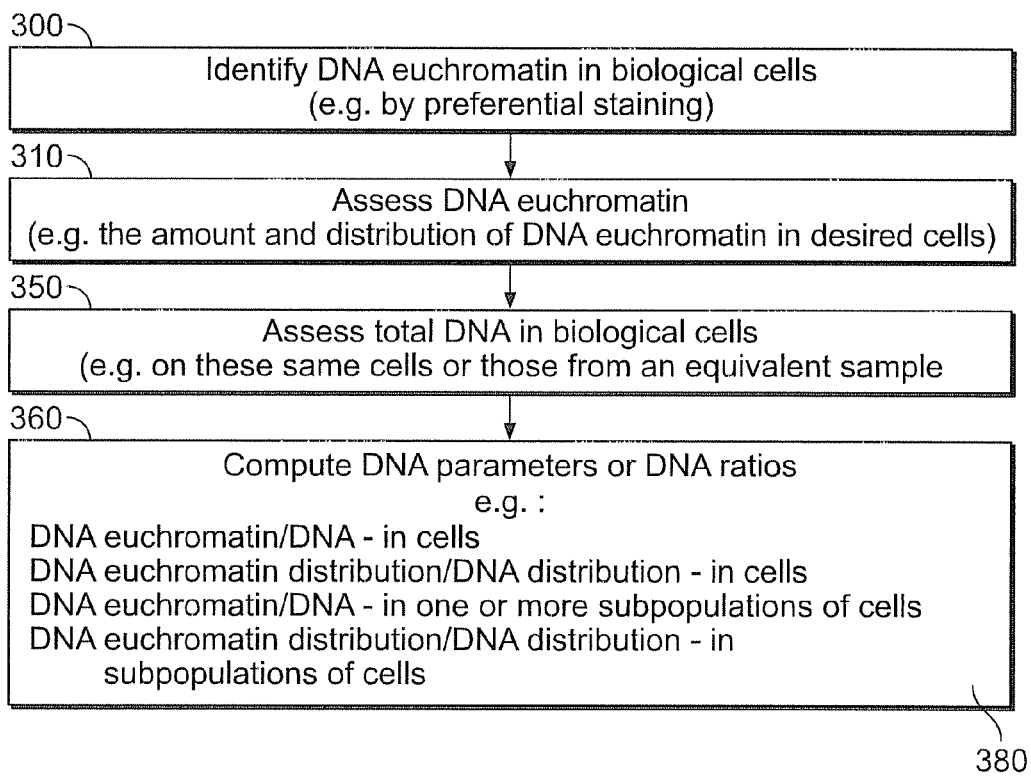
FIG. 3d: A block diagram of an embodiment of the present invention.

FIG. 3d shows yet another embodiment of the present invention further comprising the step of assessing total DNA 350 and the step of computing a DNA parameter or ratio from the measurements of the amount and distribution of euchromatin and the amount and distribution of total DNA 360. This embodiment can also include the step 380 of comparing previous data for a test case to the current results, thereby providing a sensitive means to monitor changes, for example, in RNA/protein synthesis in a particular plant, cell-line, animal or other source of biological cell. As employed with Feulgen methods, the method of the present invention goes against what is discussed in the prior art, gaining advantage by altering the hydrolysis conditions and thus deriving novel diagnostic infomation. More particularly, in one embodiment, the present method performs DNA acid hydrolysis at lower than room temperature (25 degrees Celsius) and seeks to restrict staining to DNA euchromatin (that portion of DNA most associated with protein synthesis). For example, performing a one hour acid hydrolysis in 5 N acid preferably HCl at 15 degrees Celsius followed by one hour Feulgen staining with thionin or pararosaniline as the color agent. Or, perform acid hydrolysis for a time period between one minute and two hours, preferably between 15 minutes and two hours. Or, perform acid hydrolysis at a lower acidity, such as 0.1 to 5.0 N. In addition to establishing novel hydrolysis conditions, rater than simply attempting to quantify the total amount of DNA euchromatin (which may be correlated with acid-labile DNA), in yet another embodiment of the present invention, DNA euchromatin distribution is measured on this uniquely stained DNA fraction. As cells respond to disease or chemical factors, in some instances changes in DNA synthesis may observed and measured in the DNA euchromatin of these cells. It may be useful to express such cellular responses as a value, such as CRF.

Cell suspensions are prepared from cervical or buccal mucosal scrapings, nipple aspirates, bronchial washings, sputum or other body fluids or cellular preparations of disaggregated tissue. As used herein, associated tissue means any tissue that may be expected to have cells of, or derived from the diseased tissue. For example, a sputum sample when used to test for lung cancer is defined as an associated tissue since such a sample typically contains primarily exfoliated lung cells. Similarly, use of nipple aspirate fluid would be considered an associated tissue for the detection of breast cancer. Non-associated tissue as used here in means a tissue that typically does not contain cells primarily from the disease being assessed, for example, buccal mucosa (cells form the oral cavity) as used to detect lung cancer would be considered a non-associated tissue, as would the use of voided urine or bladder washings to detect prostate cancer. When a systemic fluid such as blood, CSF, plasma etc. is being tested, it will be considered a non-associated tissue because the cancer or disease site, unless identified with another marker, or is anticipated, as in the case of recurrence, will generally be unknown. The distinction makes clear the ability and intent of the present method to detect a cellular response factor (CRF) locally in associated tissue and as a more systemic effect in non-associated tissue.

Deposited cellular material is stained using an appropriate DNA staining method and measurement tools, for example, Feulgen staining with assessment of the amount of DNA euchromatin and the distribution of DNA euchromatin made by image cytometry. DNA euchromatin may be correlated to what researchers previously called acid-labile DNA, however the present staining method establishes reaction conditions which exploit the kinetics of acid hydrolysis to target DNA euchromatin.

By general definition, the assessment of MAC requires the analysis of ostensibly normal cells. To accomplish this, DNA content must first be measured (typically as a distribution) and thresholds established (e.g. two standard deviations from the diploid peak) to group cells with a substantially normal amount of DNA. Abnormal DNA content (aneuploidy) is itself, potentially diagnostic, and therefore these cells would typically not be assessed for MAC.

The present method is further distinguished from MAC methods which require that substantially all DNA be stained. The present method is best applied to patient samples that can be expected to contain a significant population of ostensibly normal cells, which may not present a substantial limitation, even when diseased tissue is directly sampled, as with cervical scrapings for Pap screening. In many cases of cervical cancer, the appearance of a significant number of cancerous cells on the microscope slide is considered by some to be rare. For samples such as nipple aspirates for breast cancer detection, buccal mucosa for detecting lung cancer and other samples rich in exfoliated cells, these considerations do not impede exploitation of the present method, as they contain a substantial number of ostensibly normal cells. Another significant difference from other disease detection methods based on DNA content or DNA distribution is that the present invention does not generate classical DNA histograms of the cell cycle. There is no need to select DNA diploid cells for analysis since the majority of cells in appropriate samples will not be in s-phase. To improve the sensitivity or specificity of the present invention, measurement of CRF may be used in conjunction with other assays, such as DNA ploidy, MAC or other diagnostic tests. Similarly, measurement of CRF may be used to screen an at risk population to identify a more restricted population for subsequent testing, such as evaluation of cell surface markers with monoclonal antibodies or gene markers. Diagnostic assessment of DNA euchromatin (expressed for example as a CRF) may on a cell by cell basis within a test sample or may be made on a slide to slide basis between tests samples from the same source (providing a means to monitor a disease or treatment of a disease) or a CRF in a test sample may be compared to population norms or other useful target range.

The present invention, may also be used to assess how application (or removal) of influences, such as environment, radiation, chemical agents, medications, herbs, vitamins, etc., interact to effect cells, establishing uses in monitoring wellness and pharmacological screening. Additional uses include assessing age related disorders, allergies, infections, Alzheimer's disease, 'Time of Death', chronic fatigue syndrome, etc. The method may be advantageously applied to biological cells including micro-organisms, plants, animals, or cultured cells, alone or in conjunction with other markers.

As discussed in U.S. patent application Ser. No. 10/232, 698, the normalization of digital images may be used to advantage prior to the calculation of cell features. Previous methods (e.g. MAC) relied upon analysis of a DNA histogram of the cell cycle. The present method provides a unique method of digital image normalization. In addition, total DNA may be assessed providing a basis to estimate the DNA euchromatin fraction.

While preferred embodiments of the present invention are shown and described, it is envisioned that those skilled in the art may device modifications of the present invention without departing from the spirit and scope of the appended claims.

I claim:

1. A method of assessing euchromatin, comprising:
preferentially staining euchromatin in biological cells;
measuring at least one variable, said at least one variable comprising at least one of an amount of said euchromatin and a distribution of said euchromatin; and
comparing said at least one variable to a reference value, wherein the reference value represents at least one of a known amount of euchromatin and a known distribution of euchromatin in reference cells.

2. The method of claim 1, further comprising using an absorbance stain.

3. The method of claim 2, wherein said absorbance stain comprises at least one of pararosaniline, azure A, a thiazine derivative, and acriflavine.

4. The method of claim 1, further comprising using a fluorescence stain.

5. The method of claim 4, wherein said fluorescence stain comprises at least one of a propidium iodide, an adenine-thiamine selective stain, a green nucleic acid stain, and a cytosine-guanine stain.

6. The method of claim 1, further comprising using at least one of monoclonal antibody or a gene marker.

7. The method of claim 1, wherein said staining step comprises Feulgen staining.

8. The method of claim 7, wherein said Feulgen staining step ccmprises preferentially hydrolyzing said euchromatin with an acid having a concentration in the range of 0.1 to 5.0 N and performing said Feulgen staining step at less than 25 degrees Celsius.

9. The method of claim 8, wherein said hydrolyzing step is performed at approximately 15 degrees Celsius.

10. The method of claim 8, wherein said acid is hydrochloric acid.

11. The method of claim 8, wherein said hydrolyzing step is performed for one hour.

12. The method of claim 8, wherein said hydrolyzing step is performed for a time period between one minute and two hours.

13. The method of claim 8, wherein said hydrolyzing step is performed for a time period between 15 minutes and two hours.

14. The method of claim 1, further comprising assessing at least one of an amount of total DNA and a distribution of total DNA in the biological cells.

15. The method of claim 14, futher comprising computing a parameter comprising at least one of a ratio of said amount of euchromatin to said amount of total DNA and the ratio of said distribution of euchromatin to said distribution of total DNA.

16. The method of claim 15, wherein said parameter is computed for a subpopulation of the biological cells.

17. The method of claim 1, wherein said reference value is stored in a database.

18. The method of claim 1, wherein said reference value is determined from substantially healthy biological cells.

19. The method of claim 1, wherein said reference value is determined from diseased cells.

20. The method of claim 1, wherein said method is used for at least one of detecting disease, monitoring weilness, assessing bio-activity, and pharmacological screening.

21. A method of assessing euchromatin in biological cells, comprising: preferentially staining euchromatin in a first set of biological cells taken from an organism;
    measuring at least one variable, said at least one variable comprising at least one of an amount of said euchromatin and a distribution of said euchromatin in said first set of biological cells;
    expressing at least one of said measured amount and said measured distributior in said first set of biological cells as a basal cell response factor relating to said euchromatin; altering an influence on the organism;
    preferentially staining euchromatin in a second set of biological cells taken from the organism after said altering step;
    measuring at least one variable, said at least one variable comprising at least one of an amount of said euchromatin and a distribution of said euchromatin in said second set of biological cells;
    expressing at least one of said measured amount and said measured distribution in said second set of biological cells as an exposure cell response factor relating to said euchromatin; and
    comparing said basal cell response factor to said exposure cell response factor.

22. The method of claim 21, wherein said influence comprises at least one of an environment, radiation, a chemical agent a medication, an herb, and a vitamin.

23. The method of claim 21, wherein said altering step comprises reducing the organisms's exposure to said influence.

24. The method of claim 21, wherein said altering step comprises increasing the organism's exposure to said influence.

25. The method of claim 21, further comprising using an absorbance stain.

26. The method of claim 25, wherein said absorbance stain comprises at least one of pararosaniline, azure A, a thiazine derivative, and acriflavine.

27. The method of claim 21, further comprising using a fluorescence stain.

28. The method of claim 27, wherein said fluorescence stain comprises at least one of a propidium iodide, an adenine-thiamine selective stain, a green nucleic acid stain, and a cytosine-guanine stain.

29. The method of claim 21, further comprising using at least one of a monoclonal antibody or a gene marker.

30. The method of claim 21, wherein said staining step comprises Feulgen staining.

31. The method of claim 30, wherein said Feulgen staining step comprises preferentially hydrolyzing said euchromatin with an acid having a concentration in the range of 0.1 to 5.0 N and performing said Feulgen staining step at less than 25 degrees Celsius.

32. The method of claim 31, wherein said hydrolyzing step is performed at approximately 15 degrees Celsius.

33. The method of claim 31, wherein said acid is hydrochloric acid.

34. The method of claim 31, wherein said hydrolyzing step is performed for one hour.

35. The method of claim 31, wherein said hydrolyzing step is performed for a time period between one minute and two hours.

36. The method of claim 31, wherein said hydrolyzing step is performed for a time period between 15 minutes and two hours.

37. The method of claim 21, further comprising assessing at least one of an amount of total DNA and a distribution of total DNA in the biological cells.

38. The method of claim 37, further comprising computing a parameter comprising at least one of the ratio of said amount of euchromatin to said amount of total DNA and the ratio of said distribution of euchromadn to said distribution of total DNA.

39. The method of claim 38, wherein said parameter is computed for a subpopulation of the biological cells.

40. The method of claim 21, further comprising comparing at least one of said basal cell response factor and said exposure cell response factor to a reference value.

41. The method of claim 40, wherein said reference value is stored in a database.

42. The method of claim 40, wherein said reference value is determined from substantially healthy biological cells.

43. The method of claim 40, wherein said reference value is determined from diseased cells.

44. The method of claim 21, wherein said method is used for at least one of detecting disease, monitoring wellness, assessing bin-activity, and pharmacological screening.

* * * * *